(12) United States Patent
Makino (10) Patent No.: US 10,918,270 B2
(45) Date of Patent: Feb. 16, 2021

(54) ENDOSCOPE SYSTEM AND EVALUATION VALUE CALCULATION DEVICE

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 15/764,821

(22) PCT Filed: Sep. 30, 2016

(86) PCT No.: PCT/JP2016/079024
§ 371 (c)(1),
(2) Date: Mar. 29, 2018

(87) PCT Pub. No.: WO2017/057680
PCT Pub. Date: Apr. 6, 2017

(65) Prior Publication Data
US 2018/0279866 A1    Oct. 4, 2018

(30) Foreign Application Priority Data

Sep. 30, 2015    (JP) .............................. JP2015-192431

(51) Int. Cl.
*G06T 7/00*    (2017.01)
*G06T 7/80*    (2017.01)
(Continued)

(52) U.S. Cl.
CPC ........ *A61B 1/0684* (2013.01); *A61B 1/00009* (2013.01); *A61B 1/00045* (2013.01);
(Continued)

(58) Field of Classification Search
CPC ........... A61B 1/0684; A61B 1/07; A61B 1/05; A61B 1/0669; A61B 1/0646; A61B 1/045;
(Continued)

(56) References Cited

U.S. PATENT DOCUMENTS

2003/0071895 A1*  4/2003  Higuchi ................. H04N 7/183
                                                       348/65
2003/0113014 A1*  6/2003  Katoh ................... H04N 1/6083
                                                      382/167
(Continued)

FOREIGN PATENT DOCUMENTS

JP        2010-187756 A    9/2010
JP        5006759 B2        8/2012
(Continued)

OTHER PUBLICATIONS

International Search Report dated Dec. 13, 2016, issued in International Application No. PCT/JP2016/079024, 2 pages.

*Primary Examiner* — John P Leubecker
(74) *Attorney, Agent, or Firm* — Kilpatrick Townsend & Stockton LLP (57) ABSTRACT

An endoscope system, includes a light source device that emits illumination light to an object, an image obtaining part that captures light reflected at the object by an image pickup element and thereby obtains a color image including at least three color components, and an evaluation part that obtains, for each of pixels constituting the color image obtained by the image obtaining part, an evaluation result concerning a target disease based on an angle, in a color plane being defined by at least two of the at least three color components, formed between a line segment, which connects a predetermined reference point positioned on the color plane with a corresponding pixel point allocated corresponding to the each of the pixels in the color plane, and a reference axis having a correlation with the target disease. The reference axis is set to pass through the predetermined reference point.

10 Claims, 4 Drawing Sheets

(51) Int. Cl.
  *A61B 1/045* (2006.01)
  *A61B 1/06* (2006.01)
  *H04N 7/18* (2006.01)
  *G02B 23/24* (2006.01)
  *A61B 1/07* (2006.01)
  *A61B 1/05* (2006.01)
  *A61B 1/00* (2006.01)

(52) U.S. Cl.
  CPC .............. *A61B 1/045* (2013.01); *A61B 1/05* (2013.01); *A61B 1/0646* (2013.01); *A61B 1/0669* (2013.01); *A61B 1/07* (2013.01); *G02B 23/2469* (2013.01); *G06T 7/0012* (2013.01); *G06T 7/80* (2017.01); *H04N 7/183* (2013.01); *A61B 1/00186* (2013.01); *G06T 2207/10024* (2013.01); *G06T 2207/10068* (2013.01); *G06T 2207/30096* (2013.01)

(58) Field of Classification Search
  CPC ............ A61B 1/00045; A61B 1/00009; A61B 1/00186; H04N 7/183; G02B 23/2469; G06T 2207/30096; G06T 2207/10068; G06T 2207/10024; G06T 7/80; G06T 7/0012
  See application file for complete search history.

(56) References Cited

U.S. PATENT DOCUMENTS

| | | | |
|---|---|---|---|
| 2004/0156544 A1* | 8/2004 | Kajihara | H04N 1/628 382/167 |
| 2005/0190994 A1* | 9/2005 | Yamanaka | G06T 1/00 382/305 |
| 2007/0191677 A1* | 8/2007 | Nishimura | A61B 1/00009 600/109 |
| 2009/0109284 A1* | 4/2009 | Takayama | A61B 1/05 348/65 |
| 2009/0202124 A1* | 8/2009 | Matsuda | G06T 7/0012 382/128 |
| 2010/0074508 A1* | 3/2010 | Shinoda | H04N 1/6075 382/133 |
| 2010/0158330 A1* | 6/2010 | Guissin | G06K 9/00369 382/128 |
| 2010/0208047 A1 | 8/2010 | Kitamura et al. | |
| 2011/0032389 A1* | 2/2011 | Miyawaki | G06T 7/0002 348/234 |
| 2011/0157340 A1* | 6/2011 | Yamazaki | A61B 1/00009 348/61 |
| 2011/0164249 A1* | 7/2011 | Innami | A61B 1/00165 356/326 |
| 2012/0157768 A1* | 6/2012 | Saito | A61B 1/00009 600/109 |
| 2013/0051642 A1* | 2/2013 | Kanda | G06T 7/0012 382/128 |
| 2014/0320620 A1 | 10/2014 | Ikemoto et al. | |
| 2015/0193929 A1 | 7/2015 | Ikemoto | |
| 2016/0007829 A1* | 1/2016 | Chun | G06T 5/009 600/476 |
| 2016/0174886 A1* | 6/2016 | Shiraishi | A61B 5/14551 600/339 |

FOREIGN PATENT DOCUMENTS

| | | |
|---|---|---|
| JP | 2014-18332 A | 2/2014 |
| JP | 2014-213094 A | 11/2014 |

\* cited by examiner

ENDOSCOPE SYSTEM AND EVALUATION VALUE CALCULATION DEVICE

CROSS-REFERENCE TO RELATED APPLICATIONS

The present application is the National Phase application Under 35 U.S.C. § 371 of International Application No. PCT/JP2016/079024 filed Sep. 30, 2016, which claims priority to Japanese Application No. 2015-192431, filed Sep. 30, 2015, the entire contents of which are hereby incorporated by reference.

TECHNICAL FIELD

The present invention relates to an endoscope system and an evaluation value calculation device which calculates a predetermined evaluation value.

BACKGROUND ART

In general, a lesion portion shows a color different from the color of a normal mucosal tissue. In accordance with improvement of performance of a color endoscope device in recent years, it has become possible for an operator to conduct diagnosis by visually recognizing a lesion portion having a color only slightly different from the color of a normal tissue. However, in order for the operator to conduct diagnosis by visually recognizing a lesion portion precisely from a normal tissue in accordance with a slight color difference on a captured image obtained by an endoscope, the operator needs to be trained for a long period under guidance of an expert. Even for an expert, it is not easy to conduct diagnosis by visually recognizing a lesion portion based on a slight color difference, and therefore cautious work is required in the diagnosis.

In view of the above, for example, Japanese Patent Provisional Publication No. 2014-18332A (hereafter, referred to as patent document 1) describes an apparatus configured to execute scoring for a lesion portion on a captured image so as to assist diagnosis of the lesion portion by an operator. Specifically, the apparatus described in the patent document 1 executes a tone enhancement process in which a nonlinear gain is applied to pixel values of pixels constituting a captured image obtained by an endoscope so as to enhance a dynamic range in a portion around a boundary of a region including pixel values judged to be the lesion portion. The apparatus subsequently converts tone-enhanced pixel data in an RGB space defined by R, G and B primary colors into a predetermined color space, such as an HIS color space or an HSV color space, to obtain information on hue and saturation, judges whether each pixel is a pixel of the lesion portion based on the information on hue and saturation, and calculates an evaluation value (a lesion index) based on the number of pixels judged to be the lesion portion.

SUMMARY OF INVENTION

However, there is a drawback that, since a non-linear calculation process, such as a tone enhancement process and a conversion process of a color space, has a heavy processing load, execution of such a process needs a large amount of hardware resources. Furthermore, as a result of execution of the tone enhancement process, the evaluation value of the captured image fluctuates depending on capturing conditions (e.g., how illumination light impinges on an object) which affect the brightness of the image.

The present invention is made in view of the above described circumstance, and an object of the present invention is to provide an endoscope system and an evaluation value calculation device capable of suppressing a processing load for calculating an evaluation value while suppressing fluctuation of the evaluation value depending on brightness of an image.

An endoscope system provided by an embodiment of the invention, includes a light source device that emits illumination light to an object, an image obtaining part that captures light reflected at the object by an image pickup element and thereby obtains a color image including at least three color components, and an evaluation part that obtains, for each of pixels constituting the color image obtained by the image obtaining part, an evaluation result concerning a target disease based on an angle, in a color plane being defined by at least two of the at least three color components, formed between a line segment, which connects a predetermined reference point positioned on the color plane with a corresponding pixel point allocated corresponding to the each of the pixels in the color plane, and a reference axis having a correlation with the target disease. The reference axis is set to pass through the predetermined reference point.

According to the above described configuration, it becomes possible to suppress a processing load for calculating an evaluation value while suppressing fluctuation of the evaluation value depending on brightness of an image.

The reference axis in the color plane may be at least one of an axis having a correlation with the target disease of which degree of severity is a prescribed value or lower and an axis having a correlation with the target disease of which degree of severity is the prescribed value or higher.

The reference axis in the color plane may include at least a first axis having a correlation with a high seriousness disease where degree of severity of the target disease is the prescribed value or higher and a second axis having a correlation with a low seriousness disease where degree of severity of the target disease is lower than the high seriousness disease and the prescribed value or lower. In this case, the evaluation part obtains the evaluation result for the each of the pixels based on an angle formed between the line segment and at least one of the first axis and the second axis.

An example of the reference point is an intersection point between the first axis and the second axis.

The evaluation part may normalize the angle formed between the line segment and the first axis such that a normalized angle takes a maximum value when the angle formed between the line segment and the first axis is zero and takes a minimum value when the angle formed between the line segment and the first axis is equal to an angle formed between the first axis and the second axis, and may obtain the evaluation result concerning the target disease based on the normalized angle corresponding to the each of the pixels.

The endoscope system may further include a displaying part that superimposes and displays the evaluation result on the normal image obtained by the image obtaining part.

The evaluation result may concern, for example, a degree of severity of inflammation.

The first axis may be, for example, an axis having a high degree of correlation with hemoglobin color matter relative to another constituent in a body cavity.

The second axis may be, for example, an axis having a high degree of correlation with a color tone of mucous membrane in a body cavity relative to another constituent in a body cavity.

The endoscope system may further include a displaying part that superimposes and displays the evaluation result on the normal image obtained by the image obtaining part. In this case, the evaluation part may obtain an evaluation result concerning each of a plurality of target diseases, the color plane, the reference point and the reference axis may be set for the each of the plurality of target diseases. Furthermore, in this case, the displaying part may distinguishably superimpose the evaluation result concerning the each of the plurality of target diseases on the normal image on a screen.

Hue and saturation may be excepted from the color components, in other words, not included in the color components.

An evaluation value calculation device according to an embodiment of the invention, includes an allocating means that allocates a corresponding pixel point corresponding to each of pixels constituting a color image having Red, Green and Blue components in a plane including a first axis being an axis of the R component and a second axis which is an axis of the G component or the B component and is perpendicular to the first axis, the corresponding pixel point being allocated in the plane based on the Red, Green and Blue components of the corresponding pixel, an angle calculating means that sets a third axis having a high degree of correlation with a lesion portion having a highest degree of severity in the plane, and calculates, for the each of the pixels, an angle formed between the third axis and a line segment connecting a predetermined reference point positioned on the third axis with the corresponding pixel point, and an evaluation value calculating means that calculates a predetermined evaluation value for the color image based on the calculated angle corresponding to the each of the pixels.

In an embodiment of the invention, the angle calculating means may set a fourth axis having a high degree of correlation with a lesion portion having a lowest degree of severity, and may calculate the angle for the each of the pixels by setting an intersection between the third axis and the fourth axis as the reference point.

In an embodiment of the invention, the evaluation value calculating means may normalize the angle calculated by the angle calculating means such that a normalized angle takes a maximum vale when the angle calculated by the angle calculating means is zero and takes a minimum value when the angle calculated by the angle calculating means is equal to an angle between the third axis and the fourth axis, and may calculate the predetermined evaluation value for the color image based on the normalized angle corresponding to the each of the pixels.

In an embodiment of the invention, the third axis is, for example, an axis having a high degree of correlation with hemoglobin color matter relative to another constituent in a body cavity.

In an embodiment of the invention, the fourth axis is, for example, an axis having a high degree of correlation with a color tone of mucous membrane in a body cavity relative to another constituent in a body cavity.

In an embodiment of the invention, the predetermined evaluation value is, for example, a numerical value indicative of an abnormal portion in a body cavity.

In an embodiment of the invention, the evaluation value calculation device may be embedded in an electronic endoscope system.

An evaluation value calculation device according to an embodiment of the invention, includes an allocating means that allocates a corresponding pixel point corresponding to each of pixels constituting a color image having Red, Green and Blue components in a plane including a first axis being an axis of the R component and a second axis which is an axis of the G component or the B component and is perpendicular to the first axis, the corresponding pixel point being allocated in the plane based on the Red, Green and Blue components of the corresponding pixel, an angle calculating means that sets a third axis having a high degree of correlation with a lesion portion having a lowest degree of severity in the plane, and calculates, for each of the pixels, an angle formed between the third axis and a line segment connecting a predetermined reference point positioned on the third axis with the corresponding pixel point, and an evaluation value calculating means that calculates a predetermined evaluation value for the color image based on the calculated angle corresponding to the each of the pixels.

According to an embodiment of the invention, there are provided with an endoscope system and an evaluation value calculation device capable of suppressing a processing load for calculating an evaluation value while suppressing fluctuation of the evaluation value depending on brightness of an image.

DESCRIPTION OF EMBODIMENTS

Hereinafter, an embodiment of the present invention is described with reference to the accompanying drawings. In the following explanation, by way of example, an electronic endoscope system is explained as an embodiment of the invention.

Configuration of Electronic Endoscope System 1

Figure 1:
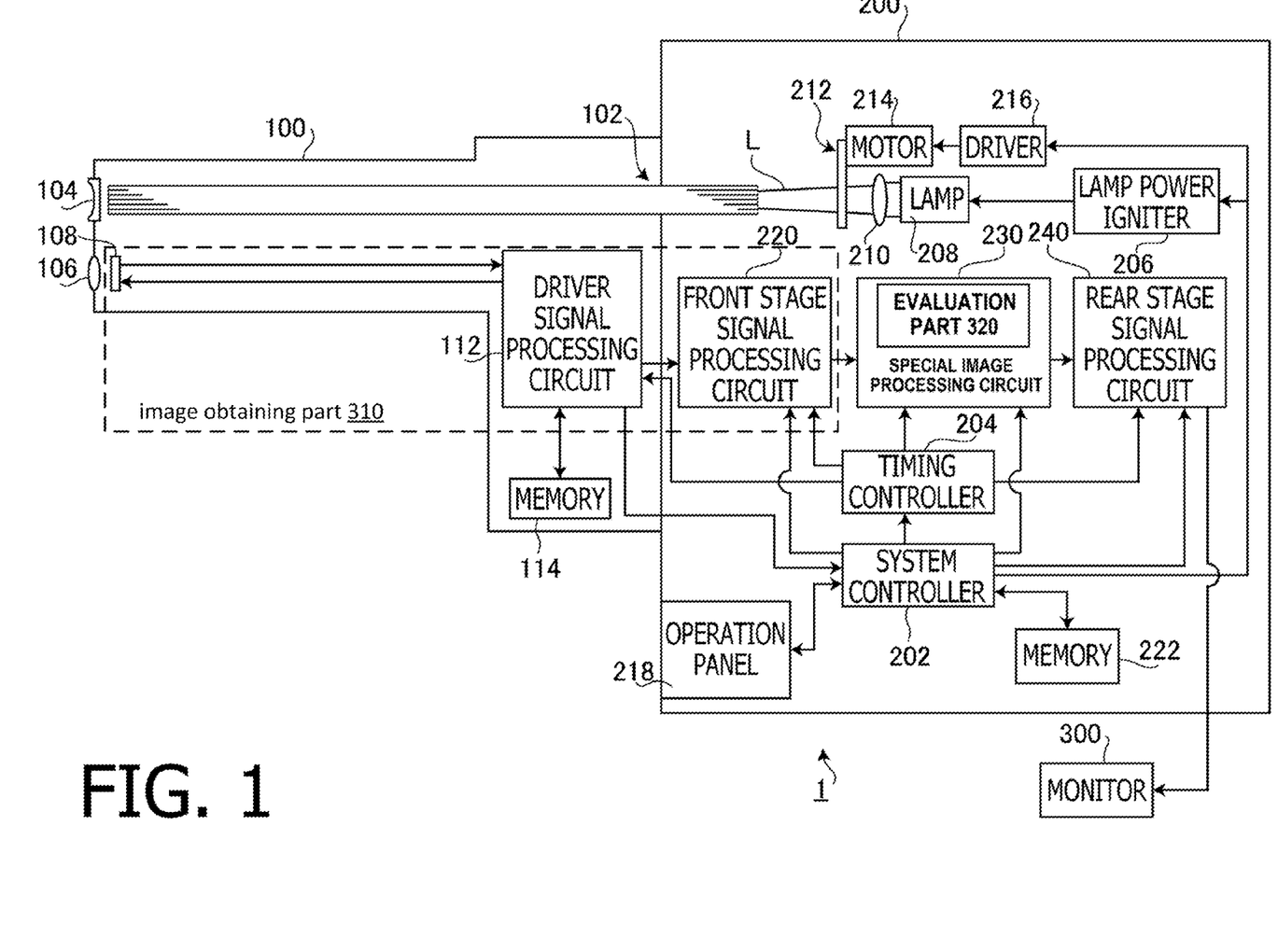
FIG. 1 is a block diagram illustrating a configuration of an electronic endoscope system according to an embodiment of the invention.

FIG. 1 is a block diagram illustrating a configuration of an electronic endoscope system 1 according to the embodiment of the invention. As shown in FIG. 1, the electronic endoscope system 1 is specifically configured for medical use and includes an electronic scope 100, a processor 200 and a monitor 300. The electronic scope 100 includes an insertion part having a distal end part and a bent portion. An LCB (Light Carrying Bundle) 102 is extended in the insertion part. There are provided with a light distribution lens 104, an objective lens 106, a solid-state image pickup device 108, etc. in the distal end part. The monitor 300 is an example of a displaying part included in the electronic endoscope system 1 according to the embodiment of the invention. In the following explanation, the electronic endoscope system shown in FIG. 1 is explained as an example of an electronic endoscope system, but the electronic endoscope system according to the present invention is not limited to that shown in FIG. 1. In the following explanation, by way of example, inflammation is explained as a target disease for calculating an evaluation value, but the target disease is not limited to inflammation. The present invention can be applied for a target disease which can be evaluated with using color components.

The processor 200 includes a system controller 202 and a timing controller 204. The system controller 202 executes various programs stored in a memory 222, and totally controls the electronic endoscope system 1. Further, the system controller 202 is connected to an operation panel 218. In accordance with an instruction inputted by an operator through the operation panel 218, the system controller 202 alters operation of the electronic endoscope system 1 and parameters for the operation of the electronic endoscope system 1. The instructions inputted by the operator include, for example, an instruction for changing operation modes of the electronic endoscope system 1. In this embodiment, the operation modes include a normal mode and a special mode. The timing controller 204 outputs clock pulses for adjusting timings of the operation to each circuit in the electronic endoscope system 1.

The electronic endoscope system 1 includes a light source device. By way of example, a lamp 208, a semiconductor light emitting element, etc. are applied as the light source device, but a type of the light source device is not limited to these. The lamp 208 shown in FIG. 1 emits white light L after being activated by a lamp power igniter 206. The lamp 208 is a high intensity lamp, such as, a xenon lamp, a halogen lamp, a mercury lamp or a metal-halide lamp. The white light L emitted by the lamp 208 is converged by a collecting lens 210 and the light amount of the white light L is limited to an appropriate amount by a diaphragm 212. It is noted that the lamp 208 may be substituted for a semiconductor light emitting element, such as, an LD (Laser Diode) or an LED (Light Emitting Diode). The semiconductor light emitting element has characteristics of low power consumption and small heat generation in comparison with other types of light sources. Therefore, using the semiconductor light emitting element is advantageous since a bright image can be obtained while suppressing the power consumption and/or heat generating amount. To be able to obtain a bright image results in improvement of accuracy of an inflammation evaluation value which will be described later. The semiconductor light emitting element may be provided with the processor 200 or the electronic scope 100. An example of the semiconductor light emitting element may be arranged in the distal end part of the electronic scope 100.

To the diaphragm 212, a motor 214 is mechanically connected via a transmission mechanism (not shown), such as an arm and gear. The motor 214 is, for example, a DC motor, and drives the diaphragm 212 under driving control of a driver 216. The diaphragm 212 is activated and a degree of opening of the diaphragm 212 is changed by the motor 214 so that the brightness of a video displayed on a display screen of the monitor 300 is kept appropriate. The amount of the white light L emitted by the lamp 208 is restricted according to the degree of opening of the diaphragm 212. An appropriate brightness reference of video is set and altered in accordance with an adjusting operation of intensity by an operator through the operation panel 218. Since dimmer control circuit for adjusting the intensity by controlling the driver 216 is well known in the art, explanations thereof will be omitted.

The white light L passed through the diaphragm 212 is converged at an entrance end face of the LCB 102 and enters the inside of the LCB 102. The white light L which has entered the inside of the LCB 102 through the entrance end face propagates through the inside of the LCB 102. The white light L which has propagated through the inside of the LCB 102 emerges from an exit end face of the LCB 102 disposed at a tip of the electronic scope 100, and illuminates a living tissue via the light distribution lens 104. Returning light from the living tissue illuminated with the white light L forms an optical image on a light-receiving surface of the solid-state image pickup device 108 via the objective lens 106.

The solid state image pickup device 108 is, for example, a single chip color CCD (Charge Coupled Device) image sensor having a Bayer type pixel array. The solid state image pickup device 108 accumulates charge according to a light amount of an optical image converged at each pixel on the light-receiving surface, and generates and outputs image signals of R (Red), G (Green) and B (Blue). In the following, the image signal of each pixel (each pixel address) sequentially outputted from the solid state image pickup device 108 is referred to as a "pixel signal". The sold state image pickup device 108 is not limited to a CCD, but may be replaced with a CMOS (Complementary Metal Oxide Semiconductor) image sensor or another type of imaging device. The solid state image pickup device 108 may be a solid state image pickup device of a type mounted with a primary color (RGB) filter or a complementary color filter. An example of the complementary color filter is a CMYG (cyan, magenta, yellow and green) filter.

Regarding the primary color (RGB) filter, since they have good coloring properties in comparison with the complementary color filter, and it is possible to improve the evaluation accuracy by using an RGB image signal, which is generated by an image pick up device provided with the primary color filter, for calculating the evaluation value. Further, by using the primary color filter, it becomes unnecessary to convert signals in an inflammation evaluation value calculation, which will be described later. Accordingly, it becomes possible to suppress the processing load in the evaluation value calculation.

In a connection part of the electronic scope 100, a driver signal processing circuit 112 is provided. To the driver signal processing circuit 112, the pixel signal of the living tissue illuminated with the white light L is input from the solid state image pickup device 118 at the frame cycle. The driver signal processing circuit 112 outputs the pixel signal from the solid state image pickup device 108 to a front stage signal processing circuit 220. In the following explanation, the "frame" may be replaced with a "field". In this embodiment, the frame cycle and the field cycle are 1/30 seconds and 1/60 seconds, respectively.

Further, the driver signal processing circuit 112 accesses a memory 114 to read unique information of the electronic scope 100. The unique information stored in the memory 114 includes, for example, the pixel number and sensitivity of the solid state image pickup device 108, available frame rates, and a model number. The driver signal processing circuit 112 outputs the unique information read from the memory 114 to the system controller 202.

The system controller 202 executes various computations based on the unique information of the electronic scope 100 and generates control signals. Using the generated control signals, the system controller 202 controls operation and timings of various circuits in the processor 200 so that appropriate processing is performed for an electronic scope connected to the processor 200.

In accordance with the timing control by the system controller 202, the timing controller 204 supplies the driver signal processing circuit 112 with clock pulses. In accordance with the clock pulses supplied from the timing controller 204, the driver signal processing circuit 112 drives and controls the solid state image pickup device 108 at timings synchronizing with the frame rate of video being processed on the processor 200 side.

Operation in Normal Mode

Signal processing operation of the processor 200 in the normal mode will now be explained.

The front stage signal processing circuit 220 executes a demosaicing process for the R, G and B pixel signals input from the driver signal processing circuit 112 at the frame cycle. Specifically, for each R pixel signal, an interpolation process by G and B peripheral pixels is executed. For each G pixel signal, an interpolation process by R and B peripheral pixels is executed. For each B pixel signal, an interpolation process by R and G peripheral pixels is executed. As a result, the pixel signals each conveying information on one color component are converted into pixel data having information on three color components of R, G and B. In this embodiment, pixel data after the demosaicing process has 8 bit (0 to 255) information for each of R, G and B components.

The front stage signal processing circuit 220 subjects the pixel data which has been subjected to the demosaicing process to predetermined signal processing, such as a matrix operation, a white balance adjustment process and a gamma correction process, and outputs the processed pixel data to a special image processing circuit 230.

The special image processing circuit 230 lets the pixel data input from the front stage signal processing circuit 220 pass through so as to be input to the rear stage signal processing circuit 240.

The rear stage signal processing circuit 240 subjects the pixel data input from the special image processing circuit 230 to predetermined image processing to generate image data for monitor representation, and converts the image data for monitor representation into a predetermined video format signal. As a result, a color image of the living tissue is displayed on the monitor 300. It is noted that the color image of the living tissue is a normal image and is constituted by at least three color components.

It is noted that the above operation of capturing an object by the solid-state image pickup device 108 and thereby obtaining the color image of the object is executed by an image obtaining part 310.

Operation in Special Mode

Next, signal processing operation of the processor 200 in the special mode will be explained.

In this embodiment, an evaluation result concerning a target disease, for each of pixels constituting the color image obtained by the image obtaining part, is obtained based on an angle, in a color plane being defined by at least two of plural color components contained in the color image of a living tissue, formed between a line segment, which connects a predetermined reference point positioned on the color plane with a corresponding pixel point allocated corresponding to the each of the pixels in the color plane, and a reference axis having a correlation with the target disease. In the following embodiment, by way of example, the color plane is defined by R component and G component and the reference axis is an axis having a correlation with inflammation diseases, but the present invention is not limited to this embodiment.

The front stage signal processing circuit 220 subjects the pixel signal which is input thereto at the frame cycle from the driver signal processing circuit 112 to predetermined signal processing, such as a demosaicing process, a matrix operation, a white balance adjustment process and a gamma correction process, and outputs the processed pixel signal to the special image processing circuit 230.

Special Image Generation Process

Figure 2:
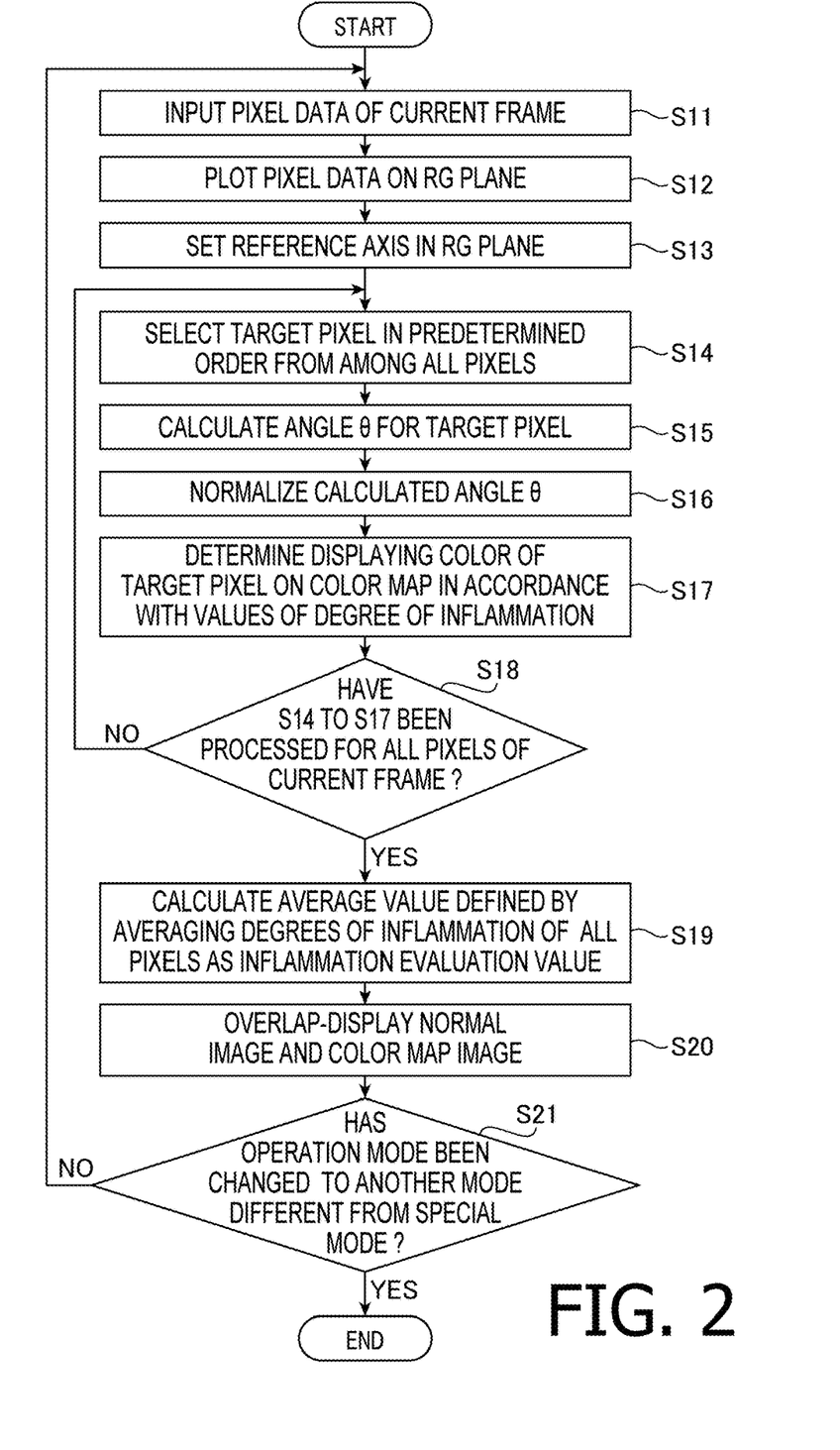
FIG. 2 is a flowchart illustrating a special image generation process executed by a special image processing circuit provided in a processor according to the embodiment of the invention.

FIG. 2 is an exemplary flowchart illustrating a special image generation process executed by the special image processing circuit 230. The special image generation process shown in FIG. 2 is started when the operation mode of the electronic endoscope system 1 is switched to the special mode.

S11 in FIG. 2 (Input of Pixel Data of Current Frame)

In step S11, pixel data of each pixel of current frame is input from the front stage signal processing circuit 220.

S12 in FIG. 2 (Plotting to RG Plane)

Figure 3:
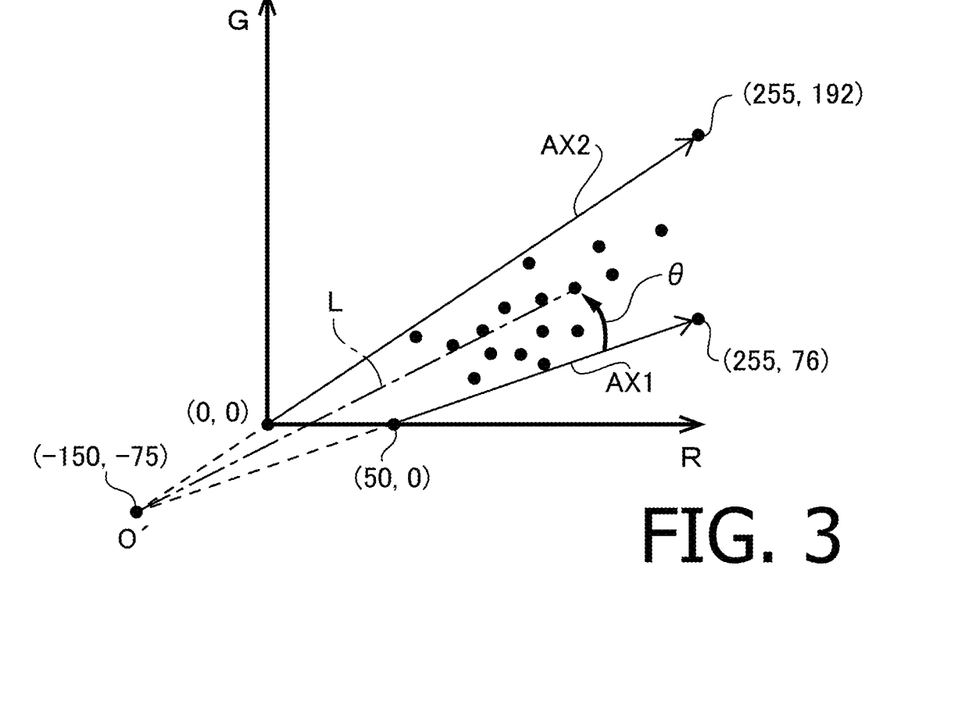
FIG. 3 is a diagram illustrating an RG plane in which corresponding pixel points are plotted according to the embodiment of the invention.

FIG. 3 represents an RG plane defined by the R axis and the G axis perpendicularly intersecting with each other, more concretely, RG plane being a plane section defined by two axes of the R axis and the G axis in the RG plane. It should be noted that the R axis is an axis for the R component (a pixel value of R), and the G axis is an axis of the G component (a pixel value of G). In step S12, the pixel data (three dimensional data) of each pixel in the RGB space defined by R, G and B primary colors is converted into two dimensional data of RG, and is plotted (orthogonally projected) in the RG plane in accordance with the R and G pixel values as shown in FIG. 3. In the following, for convenience of explanation, a point of the pixel data plotted in the RG plane is referred to as a "corresponding pixel point". In FIG. 3, for purposes of clarification of drawings, all of corresponding pixel points are not illustrated, but the corresponding pixel points are partially illustrated.

As described above, in step S12, the pixel data (three dimensional data) of the color space is orthogonally projected in the color plane. A point intersecting a perpendicular line on the color plane, the perpendicular line being extended down from a point plotted in the color space corresponding to the pixel data to the color plane, is a corresponding pixel point (two dimensional data).

S13 in FIG. 2 (Setting of Reference Axis)

Figure 4:
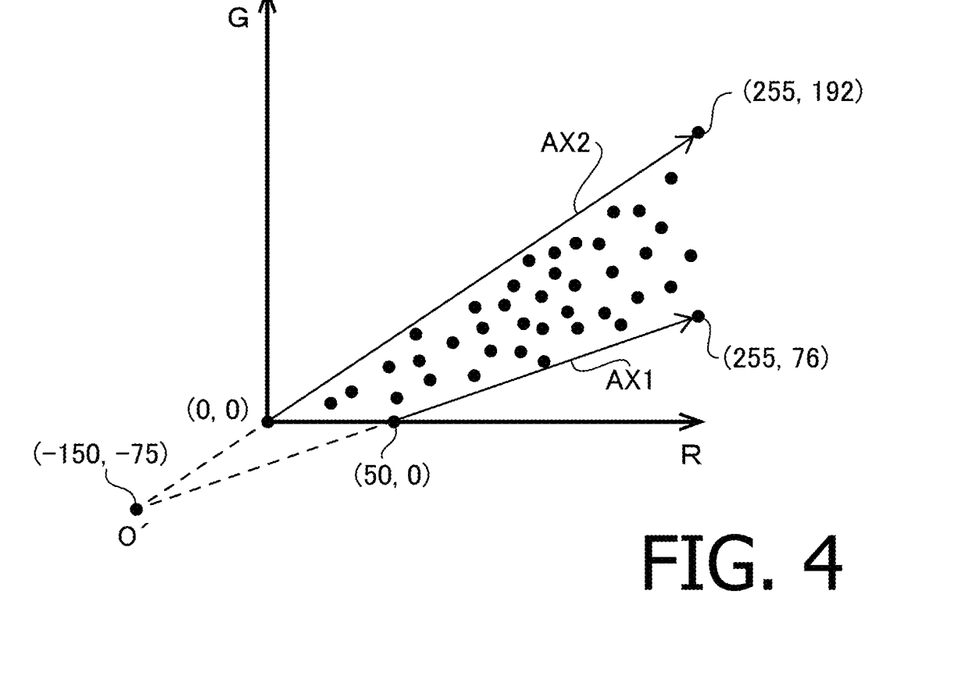
FIG. 4 is a diagram illustrating a reference axis set in the RG plane.

In step S13, a reference axis in the RG plane required for calculating a degree of inflammation is defined. FIG. 4 is a drawing supplementary illustrating the reference axis.

In a body cavity of a patient being an image capturing target, the R component is a dominant component with respect to the other components (G and B components) due to effects by hemoglobin coloring matter and etc. Typically, redness (i.e., the R component) becomes greater than the other color tones (i.e., the G and B components), as the degree of inflammation becomes stronger. However, the color tone of a captured image of the inside of the body cavity varies depending on the capturing condition affecting the brightness (e.g., how the white light L impinges on the living tissue). For example, a shaded portion to which the white light L does not reach becomes black (an achromatic color of which R, G and B values are zero or approximately zero). On the other hand, a portion on which the white light strongly impinges and which thereby causes regular reflection becomes white (an achromatic color of which the R, G and B values are 255 and approximately 255). That is, when the same abnormal portion in which inflammation occurs is captured, the pixel value of the image of the abnormal portion becomes greater as the intensity of the white light L impinging thereon becomes stronger. Therefore, depending on how the white light L impinges on the living tissue, the pixel value may take a value not correlating to the strength of inflammation.

In general, a healthy portion in a body cavity in which non inflammation is caused is covered by an adequate amount of mucous membrane. By contrast, an abnormal portion in which inflammation is caused is not covered by an adequate amount of mucous membrane. In an abnormal portion such as a lesion portion, as a degree of inflammation becomes greater, the mucous membrane becomes thinner. The mucous membrane has a color tone based on a white color, but slightly yellows. Therefore, a color tone (a yellow color tone) of the mucous membrane projected on an image changes depending on gradation of yellowing (the thickness of the mucous membrane). Therefore, it is conceivable that the gradation of a mucous membrane serves as an index for evaluating a degree of inflammation.

For this reason, in step S13, for example, a straight line passing through (50, 0) and (255, 76) in the RG plane is set as one of the reference axes, and a straight line passing through (0, 0) and (255, 192) in the RG plane is set as one of the reference axes as shown in FIG. 4. For convenience of explanation, the former reference axis is referred to as a "hemoglobin change axis AX1", and the latter reference axis is referred to as a "mucous membrane change axis AX2". Setting data of the hemoglobin change axis AX1 and the mucous membrane change axis AX2 may be previously stored, for example, in a storage medium, such as, the memory 222. As described above, (50, 0), (255, 76), (0, 0) and (255, 192) are examples of point which the reference axis is passed through, but not limited to these, may be appropriately changed to other points.

The plotting shown in FIG. 4 is obtained as a result of the inventor's analysis for a number of sample images in a body cavity. The sample images used for the inventor's analysis include inflammation image examples of various ranks, such as an inflammation image example having the highest seriousness and an inflammation image example having the lowest seriousness (which may be regarded as a substantially healthy portion). In the examples shown in FIG. 4, for purposes of clarification, a part thereof is plotted. The number of plotting obtained as the result of the inventor's analysis is extremely larger than those represented in FIG. 4.

As described above, as a degree of inflammation of an abnormal portion becomes greater, the R component becomes stronger relative to the other components (the G and B components). Therefore, of axes representing a boundary line between an area in which plotted points are distributed and an area in which no plotted point is distributed, an axis closer to the R axis (i.e., an axis on a boundary line passing through (50, 0) and (255, 76) in FIG. 4) is set as an axis having a high degree of correlation with a lesion portion having the highest degree of severity of inflammation (i.e., an inflammation (abnormal) portion having the highest degree of severity). This axis is the hemoglobin change axis AX1. On the hemoglobin change axis AX1, points which correspond to the inflammation portion having the highest degree of severity and captured in various types of conditions (e.g., a condition on how the white light L impinges on the living tissue) are plotted.

On the other hand, as a degree of inflammation becomes closer to a healthy condition, the G component (or the B component) thereof becomes stronger relative to the R component. Therefore, of axes representing a boundary line between an area in which plotted points are distributed and an area in which no plotted point is distributed, an axis on a boundary line closer to the G axis relative to the R axis (i.e., an axis on a boundary line passing through (0, 0) and (255, 192) n FIG. 4) is set as an axis having a high degree of correlation with a lesion portion of which the degree of severity is the lowest (i.e., an inflammation portion having the lowest degree of severity and can be regarded as being substantially a healthy portion). This axis is the mucous membrane change axis AX2. On the mucous membrane change axis AX2, points which correspond to the inflammation portion having the lowest degree of severity (the inflammation portion which can be regarded as being substantially a healthy portion) and captured in various types of conditions (e.g., a condition on how the white light L impinges on the living tissue) are plotted.

There are cases where an inflammation portion having the highest degree of severity causes bleeding. On the other hand, since an inflammation portion having the lowest degree of severity is substantially equal to a healthy portion, the inflammation portion of this type is covered with an adequate amount of mucous membrane. Therefore, the plotted points in the RG plane shown in FIG. 4 can be regarded as being distributed in an area surrounded by an axis having the highest degree of correlation with blood (hemoglobin color matter) and an axis having the highest correlation with the color of mucous membrane. Therefore, of boundary lines between an area in which plotted points are distributed and an area in which no plotted point is distributed, a boundary line closer the R axis (of which R component is strong) corresponds to an axis (hemoglobin change axis AX1) representing an inflammation portion having the highest degree of severity, and a boundary line closer to the G axis (of which G component is strong) corresponds to an axis (the mucous membrane change axis AX2) representing an inflammation portion having the lowest degree of severity.

In the above embodiment, the reference axes are examples of the axis representing an inflammation portion having the highest degree of severity and the axis representing an inflammation portion having the lowest degree of severity, but not limited to these.

The reference axis may be at least, for example, an axis having a correlation with inflammation of an evaluation object. By way of example, at least one of axes, the axes include an axis having a correlation with a pixel, the pixel representing an portion where degree of severity of inflammation is a prescribed value or lower and an axis having a correlation with a pixel, the pixel representing an portion where degree of severity of inflammation is a prescribed value or higher, may be set as the reference axis.

In the case where the portion where degree of severity of inflammation is a prescribed value or higher corresponds to a portion of high seriousness inflammation and the portion where degree of severity of inflammation is a prescribed value or lower and is lower than the high seriousness inflammation, an axis representing the portion of high seriousness inflammation and an axis representing the portion of low seriousness inflammation may be set as the reference axis.

In the case where a plurality of the reference axes are set, it is preferable that an angle formed between the plurality of the reference axes is less than an angle formed between the axes representing the color components which define the color plane. As the angle formed between the reference axes become smaller, it is capable of obtaining more accurately evaluation value by improving its resolution. The angle formed between the reference axes is preferably less than 90 degrees, and more preferably 60 degrees or lesser.

S14 in FIG. 2 (Selection of Target Pixel)

In step S14, a target pixel is selected in predetermined order from among all the pixels.

S15 in FIG. 2 (Calculation of Angle)

In step S15, for the target pixel selected in step S14 (selection of target pixel), an angle for calculating the degree of inflammation is calculated. Specifically, in step S15, an angle θ formed between the hemoglobin change axis AX1 and a line segment L connecting an intersection (reference point) O' between the hemoglobin change axis AX1 and the mucous membrane change axis AX2 with a corresponding pixel point of the target pixel is calculated (see FIG. 3). The reference point O' is positioned at the coordinate (−150, −75).

As described above, by way of example, the reference point O' is positioned at coordinate (−150, −75), but not limited to this, may be appropriately changed to another coordinate point.

It is noted that the reference point causes to suppress errors of the evaluation result depending on fluctuation of brightness of an image by positioning at a preferable coordinate point. More concretely, it is preferable that a point minimizing errors between an evaluation result corresponding to dark parts (whose brightness of the image are below a prescribed value) and an evaluation result corresponding to non-dark parts (whose brightness of the image are beyond the prescribed value) is preliminarily determined and set as the reference point.

By way of example, when the reference point O' is set at between coordinate (−10, 10) and coordinate (10, 10), it is possible to obtain an accurate evaluation result, since variation of angle θ depending on a change of the corresponding pixel point is greater and the resolution is more improved than when coordinate (−150, 75) being set as the reference point O'.

On the other hand, when the reference point O' may be set at between coordinate (−50, −50) and coordinate (−200, −200), it is possible to suppress effects by noise included in the evaluation result which is obtained by an evaluation part 320.

S16 in FIG. 2 (Normalization)

When the brightness of the captured image in the body cavity changes depending on how the white light L impinges on the living tissue of the body cavity, while being affected by individual differences of patients, captured parts in the body cavity and inflammatory conditions, the color of the captured image, in the RG plane, generally changes along the hemoglobin change axis AX1 in an inflammation portion having the highest degree of severity and changes along the mucous membrane change axis AX2 in an inflammation portion having the lowest degree of severity. Furthermore, it is expected that the color of an inflammation portion having an intermediate degree of severity may change in a similar manner. That is, when the condition on how the white light L impinges thereon changes, the corresponding pixel point corresponding to an inflammation portion shifts in an azimuth angle direction whose basic point is the reference point O'. In other words, when the condition on how the white light impinges thereon changes, the corresponding pixel point in an inflammation portion moves while maintaining the angle θ and the distance between the reference point O' and the corresponding pixel point changes. This means that the angle θ is a parameter which is not substantially affected by the brightness of the captured image.

As the angle θ becomes smaller, the R component becomes stronger relative to the G component, and this means that the degree of severity of the inflammation portion is high. Furthermore, as the angle θ becomes larger, the G component becomes stronger relative to the R component, and this means that the severity of the inflammation portion is low. For this reason, in step S16, the angle θ is normalized such that the angle θ takes a value 255 when the angle θ is zero, and takes a value zero when the angle θ is $\theta_{MAX}$. $\theta_{MAX}$ is equal to an angle formed between the hemoglobin change axis AX1 and the mucous membrane change axis AX2. As a result, the degree of inflammation (8 bit information) falling within the range of 0 to 255 is obtained for a target pixel.

S17 in FIG. 2 (Determination of Displaying Color on Color Map)

In this embodiment, a color map image, which is obtained by mosaicking the captured image with colors in accordance with the degree of inflammation, can be displayed. In order to making it possible to display the color map image, a table in which values of the degree of inflammation and predetermined colors are associated with each other has been stored in a memory area, such as the memory 222. For example, in the table, different colors are assigned at the intervals of 5. In exemplary example, yellow color is assigned to the range of the values of the degree of inflammation 0 to 5, and different colors are assigned at the interval of 5 which is incremented in the order of color arrangement of the hue circle. Red color is assigned to the range of the value of 250 to 255.

In step S17, the displaying color of the target pixel on the color map image selected in step S14 (selection of target pixel) is set to a color corresponding to the value of the degree of inflammation of the target pixel obtained in step S16 (normalization) based on the above described table.

S18 in FIG. 2 (Judgment on Completion of Execution of Process for all Pixels)

In step S18, it is judged whether the steps S14 to S17 have been processed for all the pixels of the current frame.

If a pixel for which the steps S14 to S17 have not been processed remains (S18: NO), the special image generation process shown in FIG. 2 returns to step S 14 (selection of target pixel) to execute the steps S14 to S17 for a next target pixel.

Step S19 is executed when it is judged that the steps S14 to S17 have been processed for all the pixels of the current frame in step S18 (judgment on completion of execution of process for all pixels) (S18: YES). In step S19, the average value defined by averaging the degrees of inflammation of all the pixels of the current frame is calculated as the inflammation evaluation value of the whole captured image, and display data (for example, "Score: ○○") for the calculated inflammation evaluation value is generated. It is noted that the above operation of obtaining the inflammation evaluation value as an evaluation result concerning the target disease is executed by an evaluation part 320.

S20 in FIG. 2 (Overlay Process)

In step S20, using, as a coefficient, a ratio for overlapping a normal image based on the pixel data (i.e., pixel data having three color components of RGB) input from the front stage signal processing circuit 220 and the color map image based on the pixel data to which the predetermined colors are assigned in step S17 (determination of displaying color on color Map), the former pixel data (the normal pixel data) and the latter pixel data (the color map pixel data) are added together. The coefficient can be altered through a user operation as the need arises. When it is necessary to display the normal image deeper, the coefficient for the normal image is set to have a higher value. On the other hand, when it is necessary to display the color map image deeper, the coefficient for the color map pixel data is set to have a higher value.

S21 in FIG. 2 (Termination Judgment)

In step S21, it is judged whether the operation mode of the electronic endoscope system 1 has been changed to another mode different from the special mode. When it is judged that the operation mode has not been changed to another mode (S21: NO), the special mode generation process shown in FIG. 2 returns to step S11 (input of pixel data of current frame). On the other hand, when it is judged that the operation mode has been changed to another mode (S21: YES), the special mode generation process shown in FIG. 2 is terminated.

Screen Display Example

The rear stage signal processing circuit 240 generates an overlaid image of the normal image and the color map image based on the pixel data subjected to the adding process in step S20 (Overlay Process), and executes a masking process in which a peripheral area (a periphery of an image displaying area) of the displayed image is masked. Further, the rear stage signal processing circuit 240 generates the image data for monitor representation in which the evaluation value of inflammation is overlaid on a masking area generated by the masking process. The rear stage signal processing circuit 240 converts the generated image data for monitor representation into a predetermined video format signal, and outputs the video format signal to the monitor 300.

Figure 5:
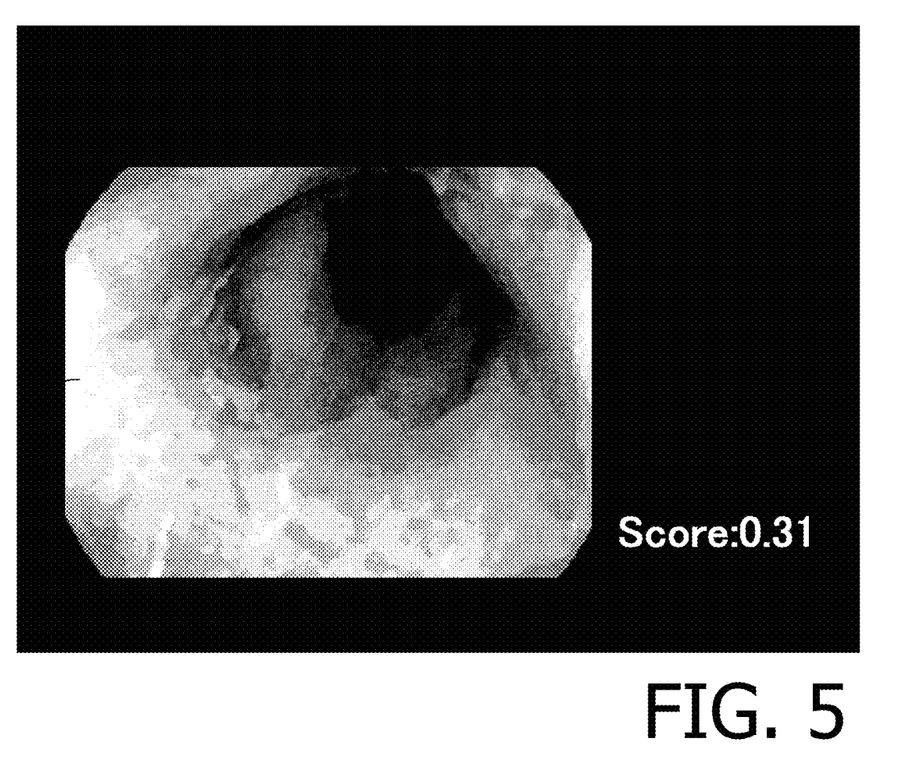
FIG. 5 illustrates an example of onscreen representation in a special mode according to the embodiment of the invention.

FIG. 5 illustrates an example of onscreen representation in the special mode. As shown in FIG. 5, on the display screen of the monitor 300, the captured image (the overlaid image in which the normal image and the color map image are overlaid) in the body cavity is displayed in a central portion and the peripheral portion of the image displaying area is masked. Further, in the masked area, the evaluation value (a score) of inflammation is displayed.

As described above, according to the embodiment, the evaluation value of inflammation (in this example, a value correlating to increase/decrease of hemoglobin color matter in a captured area) can be obtained by executing a simple calculation without executing a non-linear calculation such as a tone enhancement process and a complicated color space conversion process. That is, hardware resources required for calculation of the evaluation value of inflammation can be reduced significantly. Furthermore, since the evaluation value of inflammation does not substantially fluctuate depending on the capturing condition (e.g., how illumination light impinges on an object) which would affect the brightness of the captured image in a body cavity, the operator is able to make an accurate and objective judgment regarding inflammation.

The electronic endoscope system according to the embodiment brings following effects and solution of problems in the field of the present technique as described below.

Firstly, the electronic endoscope system according to the present embodiment serves as diagnosis support for early detection of inflammatory disease.

Secondary, according to the configuration of the present embodiment, degree of inflammation is displayed on a screen, or an image of an area where inflammation occurs is highlighted so that an operator can discover mild inflammation which is hardly recognized visually. In particular, since the mild inflammation is difficult to be discriminated from a normal area, the effects brought by the configuration of the present embodiment regarding the evaluation of the mild inflammation are significant.

Thirdly, according to the configuration of the present embodiment, it becomes possible to supply an objective evaluation value to an operator as evaluation of the degree of the inflammation, differences of diagnosis among a plurality of operators can be reduced. In particular, it is highly advantageous that the objective evaluation value, according to the configuration of the present embodiment, can be supplied to an inexperienced operator.

Fourthly, according to the configuration of the present embodiment, since an inflammation area can be displayed as an image in real time since load to image processing is reduced, diagnosis accuracy can be improved.

Fifthly, according to the configuration of the present embodiment, since the load to the calculation of the evaluation value is lightened in comparison with the background technique mentioned above, a color map image (i.e., an image indicating the degree of inflammation) and a normal image can be displayed side by side, or in a synthesized manner without delay. As a result, it becomes possible to display the color map image without extending a diagnosis time period, and further, it becomes possible to avoid increase of burden to a patient.

The target areas of an observation according to the present embodiment include, for example, respiratory organs, digestive organs and the like. The respiratory organs include, for example, lungs, ears, a nose and a throat. The digestive organs include, for example, a large bowel, a small bowel, a duodenum, and an uterus. It appears that the electronic endoscope system according to the present embodiment has a significant effect when an observation target is the large bowel. It is so because of, concretely, the following reason.

Regarding the large bowel, there are disease which can be evaluated based on the inflammation, and the advantage of discovering the inflammation area is larger in comparison of the other organs. Particularly, the inflammation evaluation value according to the present embodiment is effective as an index of inflammatory bowel disease (IBD) which is represented by the ulcerative colitis. Since no treatment method has been established for the ulcerative colitis, it is highly effective to discover the same and suppress advancing of the disease with use of the electronic endoscope system according to the configuration of the present embodiment.

Since the large bowel is an organ which is relatively narrow and long organ in comparison with a stomach, an obtained image thereof has a depth, and the deeper a portion of the image is, the darker the image is. According to the configuration of the present embodiment, it is possible to suppress variation of the evaluation value due to variation of the brightness in the image, a significant effect can be achieved by the present embodiment if the electronic endoscope system according to the present embodiment is applied to observation of the large bowel. Thus, it is preferable that the electronic endoscope system according to the present embodiment is of the respiratory organ or the digestive organ, and more preferably, of the large bowel.

It is generally difficult to diagnose a mild inflammation. However, according to the configuration of the present embodiment, for example, by displaying a result of evaluation of the degree of the inflammation, it becomes possible avoid a case where an operator overlooks the mild inflammation. In particular, concerning the mild inflammation, a fact that decision criteria thereof are not clear is a definite factor to increase individual differences of diagnoses among operators. Regarding this point, according to the configuration of the present embodiment, an objective evaluation value can be supplied to the operators, variations of diagnosis among operators can be reduced.

The above-described configuration of the present embodiment can be applied to calculation of evaluation values of not only the degree of inflammation, but various lesions associated with color change such as cancers and polyps, and advantageous effects as those described above can be brought. That is, the evaluation values according to the present embodiment are preferably evaluation values of the lesions associated with the color change, and preferably include the evaluation value of at least one of the degree of inflammation, the cancers and the polyps.

The foregoing is the explanation about the embodiment of the invention. The invention is not limited to the above described embodiment, but can be varied in various ways within the scope of the invention. For example, embodiments of this application include a combination of the embodiments explicitly described in this specification or embodiments easily realized from the above described embodiment.

In the above described embodiment, the inflammation evaluation value is calculated using R and G components contained in each pixel, however, in another embodiment, instead of using the R and G components, the R and B components may be used and thereby an evaluation value concerning another type of examination target different from that of the above described embodiment may be calculated. In such a case, since, for example, distribution of plotting of sample images are different from those shown in FIG. 4, reference axes to be set in step S13 (setting of reference axis) in FIG. 2 are also different from those illustrated in the above described embodiment.

In the above-described embodiment, the evaluation values of the inflammation and the like are calculated using the R, G and B primary color components. However, a configuration of calculating the evaluation value according to the present invention needs not be limited to usage of the R, G and B primary color components. Instead of using the R, G and B primary color components, for example, C (cyan), M (magenta), Y (yellow) and G (green) complementary color components may be used, and the evaluation value of the inflammation and the like may be calculated according to the method similar to that employed in the above-described embodiment.

In the above-described embodiment, the pixel data of each pixel in the RGB color space are converted into the pixel data in the RG plane and the inflammation evaluation value is calculated using R and G components contained in the converted pixel data. However, in another embodiment, instead of using the RGB color space, another color space (which is defined by n (n≥3) kinds of color components), such as, a CIE 1976 L*a*b* color space, a CIE LCh color space, CIE 1976 L*u*v* color space, an HSB color space, an sRGB color space, a CMK color space, a CMYK color space and a CMYG color space, may be used and pixel data of each pixel in the other color space may be converted into pixel data in a color space which has lower dimension than the other color space and is defined by m (n (n>m≥2) kinds of color components. With using the pixel data in the lower dimensional color space obtained by converting the pixel data in the other color space, an evaluation value concerning another type of target disease corresponding to the other color space (atrophy of stomach, tumor of large bowel, etc.) different from that of the above described embodiment may be calculated.

It is preferable to appropriately select and set the reference axis according to, for example, a color space, a color plane, type of a disease of an evaluation object. The reference axis may be set as an axis passing through coordinate (0, 0) in the color plane, whereby mounting on a device can be efficiently simplified.

In the above-described embodiment, a light source device including the lamp power igniter 206, the lamp 208, the collecting lens 210, the diaphragm 212, the motor 214 and the like is provided to the processor integrally therewith. However, the light source device may be provided as a device separated from the processor.

As described in the above-mentioned embodiment, instead of the CCD image sensor, the CMOS image sensor may be used as the solid state image pickup device 108. The CMOS image sensor generally has a tendency that the image becomes entirely darker in comparison with the CCD image sensor. Therefore, the advantageous effect of suppressing variation of the evaluation value depending on the brightness of the image according to the configuration of the above-described embodiment is exhibited more significantly in a case where the CMOS image sensor is used as the solid state image pickup device.

In order to perform diagnosis accurately, it is preferable to obtain a high-resolution image. Therefore, in view of improving the diagnosis accuracy, it is preferable that the resolution of the image is one million pixels or more, more preferable the resolution if two million pixels or more, and still further preferable the resolution is eight million pixels or more. The higher the resolution of the image is, the heavier the processing load for executing the above-described evaluation calculation for all the pixels is. However, according to the configuration of the above-described embodiment, the processing load can be suppressed, and the advantageous effects according to the configuration of the present embodiment in processing the high-resolution image are exhibited significantly.

In the special image processing according to the above-described embodiment, all the pixels in the image are subject to the image processing. However, pixels of extremely high brightness and extremely low brightness may be excluded from those subject to the processing. Specifically, for example, by making the pixels having brightness determined to be within a predetermined reference brightness range be subject to the evaluation value calculation, it becomes possible to improve accuracy of the evaluation values.

As mentioned in the above-described embodiment, various types of light sources can be used as the light source employed in the endoscope system 1. On the other hand, there could be a case where the type of the light source is limited (e.g., the laser being excluded as the type of the light source) depending on a purpose of observation of the endoscope system 1.

Regarding the color components used for calculating the evaluation value, there could be a case where calculation of the evaluation value without using hue and saturation.

In the above described embodiment, the inflammation evaluation value is calculated based on the angle θ which is calculated as an angle formed between the hemoglobin change axis AX1 and the line segment L connecting the reference point O' and the corresponding pixel point of the target pixel, however, the present invention is not limited to such an example. For example, an angle between the line segment L and the mucous membrane change axis AX2 may be calculated and the inflammation evaluation value may be calculated based on the calculated angle. In such a case, as the calculated angle becomes smaller, the G component becomes greater relative to the R component, which means that the degree of severity of the inflammation portion is low. On the other hand, as the calculated angle becomes larger, the R component becomes greater relative to the G component, which means that the degree of severity of the inflammation portion is high. Therefore, in the step S16 (normalization) in FIG. 2, the calculated angle is normalized such that the normalized angle takes a value of zero when the calculated angle is zero, and the normalized angle takes a value of 255 when the calculated angle is $\theta_{MAX}$.

That is, the reference axis in the color plane may be at least one of an axis having a correlation with the target disease of which degree of severity is a prescribed value or lower and an axis having a correlation with the target disease of which degree of severity is the prescribed value or higher. More concretely, the reference axis in the color plane may include at least a first axis having a correlation with a high seriousness disease where degree of severity of the target disease is the prescribed value or higher and a second axis having a correlation with a low seriousness disease where degree of severity of the target disease is lower than the high seriousness disease and the prescribed value or lower. In this case, an evaluation part obtaining evaluation result is configured to obtain the evaluation result for the each of the pixels based on an angle formed between the above line segment (which connects a predetermined reference point positioned on the color plane, the color plane being defined by at least two of plural color components contained in the color image of the living tissue, with a corresponding pixel point allocated in the color plane, the corresponding pixel point corresponding to each of pixels constituting the color image obtained by the image obtaining part) and at least one of the first axis and the second axis.

Furthermore, in the above described embodiment, the intersection between the hemoglobin change axis AX1 and the mucous membrane change axis AX2 is set as the reference point O' in order to suppress the effect on the inflammation evaluation value due to brightness of a captured image, however, the present invention is not limited to such a configuration. For example, the origin point (0, 0) in the RG plane positioned on the mucous membrane change axis AX2 may be set as the reference point O'. In this case, since a single axis (i.e., the mucous membrane change axis AX2) suffices for the required reference axis, the processing load of the special image generation process shown in FIG. 2 is reduced, and thereby the processing speed can be enhanced.

The evaluation part may be configured to obtain each of evaluation results concerning a plurality of target diseases. In this case, the color plane, the reference point and the reference axis would be set for each target disease. Furthermore, in this case, a monitor including a displaying part may distinguishably superimposes a plurality of evaluation results on the normal image on the screen. According to such a configuration, an operator can recognize portion which has the possibility of various kinds of diseases on the same screen without changing, for example, display image setting. As a result, it is possible to assist diagnosis by the operator, without increasing a patient's burden.

EXPLANATION OF REFERENCES

1 Electronic Endoscope System
100 Electronic Scope
102 LCB
104 Light Distribution Lens
106 Objective Lens
108 Solid-State Image Pickup Device
112 Driver Signal Processing Circuit
114 Memory
200 Processor
202 System Controller
204 Timing Controller
206 Lamp Power Igniter
208 Lamp
210 Collecting Lens
212 Diaphragm
214 Motor
216 Driver
218 Operation Panel
220 Front Stage Signal Processing Circuit
222 Memory
230 Special Image Processing Circuit
240 Rear Stage Signal Processing Circuit

The invention claimed is:

1. An endoscope system, comprising:
   a light source device configured to emit illumination light to an object;
   an image obtaining part configured to capture light reflected at the object by an image pickup element and thereby obtain a color image including at least three color components; and
   an evaluation part configured to obtain, for each of pixels constituting the color image obtained by the image obtaining part, an evaluation result concerning a target disease based on an angle, in a color plane defined by at least two of the at least three color components, formed between a line segment, which connects a predetermined reference point positioned on the color plane with a corresponding pixel point allocated corresponding to the each of the pixels in the color plane, and a reference axis having a correlation with the target disease,
   wherein the reference axis is set to pass through the predetermined reference point.

2. The endoscope system according to claim 1, wherein the color plane defined by at least two of the at least three color components is an RG plane defined by a red component and a green component among the at least three color components, and wherein the reference axis is one among a first axis that corresponds to a color of hemoglobin color matter and a second axis that corresponds to a color tone of mucous membrane in a body cavity, and wherein the predetermined reference point is an intersection point between the first axis and the second axis.

3. The endoscope system according to claim 2, wherein the first axis has a correlation with a maximum degree of the target disease and wherein the second axis has a correlation with a minimum degree of the target disease.

4. The endoscope system according to claim 3, wherein the first axis has a correlation with a first degree of the target disease that is at or above a first prescribed value and the second axis has a correlation with a second degree of the target disease that is at or below a second prescribed value, the second degree being lower than the first degree, wherein the evaluation part is configured to obtain the evaluation result for the each of the pixels based on an angle formed between the line segment and at least one of the first axis and the second axis.

5. The endoscope system according to claim 2, wherein the first axis has a correlation with a first degree of the target disease that is at or above a first prescribed value and the second axis has a correlation with a second degree of the target disease that is at or below a second prescribed value, the second degree being lower than the first degree, and wherein the evaluation part is configured to obtain the evaluation result for the each of the pixels based on an angle formed between the line segment and at least one of the first axis and the second axis.

6. The endoscope system according to claim 5, wherein the evaluation part is configured to normalize the angle formed between the line segment and the first axis such that a normalized angle takes a maximum value when the angle formed between the line segment and the first axis is zero and takes a minimum value when the angle formed between the line segment and the first axis is equal to an angle formed between the first axis and the second axis, and obtains the evaluation result concerning the target disease based on the normalized angle corresponding to the each of the pixels.

7. The endoscope system according to claim 5, wherein the evaluation part is configured to normalize the angle formed between the line segment and the first axis such that a normalized angle takes a maximum value when the angle formed between the line segment and the first axis is zero and takes a minimum value when the angle formed between the line segment and the first axis is equal to an angle formed between the first axis and the second axis, and wherein the evaluation part is configured to obtain the evaluation result concerning the target disease based on the normalized angle corresponding to the each of the pixels.

8. The endoscope system according to claim 2, further comprising a displaying part configured to superimpose and display the evaluation result on the color image obtained by the image obtaining part.

9. The endoscope system according to claim 2, wherein the evaluation result concerns a degree of inflammation.

10. The endoscope system according to claim 2, further comprising a displaying part configured to superimpose and display the evaluation result on the color image obtained by the image obtaining part, wherein the evaluation part is configured to obtain an evaluation result concerning each of a plurality of target diseases, wherein the target disease is one among the plurality of target diseases, and wherein the RG plane, the predetermined reference point and the reference axis are set for the each of the plurality of target diseases, and wherein the displaying part is configured to distinguishably superimpose the evaluation result concerning the each of the plurality of target diseases on the color image on a screen.

\* \* \* \* \*